United States Patent [19]

Chang et al.

[11] Patent Number: 5,795,996
[45] Date of Patent: Aug. 18, 1998

[54] METHOD AND APPARATUS FOR MONITORING WATER QUALITY

[75] Inventors: Chen-Chang Chang; Shu-Fei Chan; Dong-Yuan Lin; Jen-Chung Chen, all of Hsinchu; Guo Chen Chen, Taipei; Don H. C. Chen, Taipei-Hsien, all of Taiwan

[73] Assignee: Industrial Technology Research Institute, Hsinchu, Taiwan

[21] Appl. No.: 884,850

[22] Filed: Jun. 30, 1997

[51] Int. Cl.[6] .......................... G01N 33/00; G01N 22/00; G01N 31/16; B01D 21/30
[52] U.S. Cl. .......................... 73/61.41; 210/143; 422/62; 436/163
[58] Field of Search ................. 73/61.41, 53.01; 210/96.1, 143, 743, 746; 422/62; 436/163

*Primary Examiner*—Hezron E. Williams
*Assistant Examiner*—Jay L. Politzer
*Attorney, Agent, or Firm*—Beveridge, DeGrandi, Weilacher & Young LLP

[57] ABSTRACT

A method for monitoring water quality including deriving calcium hardness and M alkalinity from the linear functional relation between calcium hardness and specific conductivity, and that between log value of M alkalinity and pH value, simplifying the temperature curve into a formula, and calculating directly the saturation index. A multipurpose and inexpensive automatic water quality monitoring apparatus that can be adapted for use in cooling towers, swimming pools, and boilers may be made from a combination of an conductivity meter, pH meter, and oxidation reduction potential meter commonly used in testing, and a simple algorithm of a central processing unit.

17 Claims, 6 Drawing Sheets

METHOD AND APPARATUS FOR MONITORING WATER QUALITY

BACKGROUND OF THE INVENTION

1. Field of the Invention

The present invention relates generally to a method and apparatus for monitoring water quality, and more particularly to a method and apparatus for monitoring water quality having multiple functions.

2. Description of the Prior Art

Of the total water consumption in manufacturing factories, water used for cooling purposes has occupied a large proportion. Therefore, from the perspective of cost saving or environmental protection, it is an important issue to control the quality of cooling water to enhance the cycles of concentration and reduce the amount of water discharged. Control of water quality may further prevent scaling and corrosion, which may lead to blocking of pipes, and breaking of pipes. Control of cooling water quality may thus prevent any possible accidents or disasters arising from breaking of pipes.

At present, whether or not water quality monitoring is delegated to professional water treatment companies, the initial step in water quality monitoring is to sample water at the site and take the sample back to the laboratory.

The testing procedures at the laboratory includes: First, testing the pH value, calcium ion concentration and M alkalinity in the sample water; second, looking up relevant data or tables according to the tested values; and third, finding out the saturation index, which is very troublesome to calculate.

With the conventional testing methods and procedures, time will be wasted in going to the site to sample the water. Generally, it will take several hours from sampling to the coming out of the test result. If the job is carried out by professional water treatment companies, the result will not be known until the following day. The delay of time during the whole process will inevitably pose an obstacle to immediate remedy in water quality monitoring.

Although it has been considered to install testing apparatus at the sampling site to permit on-line testing and analysis, it is an impractical idea.

The current methods of analyzing calcium hardness include Atom Absorption (AA), Induced Coupled Plasma (ICP), Ion Chromatography (IC). But methods applicable for on-line testing have to utilize apparatus using calcium ion electrode to test calcium hardness, which is very costly. Besides, since the quality of water being tested is poorer than that of pure water, the testing electrode is prone to damage and requires frequent cleaning, maintenance and even correction of tested values, which is very inconvenient.

In addition, methods of analyzing M alkalinity are methyl orange colorimetric methods, charge balance methods, and automatic titration methods. Among these, automatic titration instruments for testing M alkalinity are very expensive, and require regular refill of testing chemicals, which is also not economical. The need to frequently refill testing chemicals has from adopting this method.

Another problem with conventional methods of water quality testing is that they can only cover such items as specific conductivity and pH values. Very rarely, some methods are able to use oxidation reduction potential to control free chlorine content in water so as to maintain disinfection effects. As regards saturation index, which is an important reference index in exhibiting the inclination to scaling and risks of corrosion, no single instrument can instantly find out. The trouble of referring to relevant tables or charts makes it difficult to instantly obtain the saturation index. This is also the reason why there is no such products available in the marketplace.

SUMMARY OF THE INVENTION

A primary object of the present invention is to provide a method for monitoring water quality by use of a water quality simulation system so as to understand change in water quality.

Another object of the present invention is to provide a method and apparatus for monitoring water quality which may find out the inter-relationship among calcium ions, M alkalinity, specific conductivity, pH values, and temperature, so as to replace hardware equipment such as testing instruments with functional relations.

A further object of the present invention is to provide a method and apparatus for monitoring water quality which may instantly reflect the saturation index of water quality so as to enhance the techniques and quality of instant water quality testing.

In order to attain the above-mentioned objects, a multipurpose and inexpensive automatic water quality monitoring apparatus that may be adapted for use in cooling water towers, swimming pools, and boilers can be achieved using a conductivity meter, a pH meter, and an oxidation reduction potential meter commonly used in testing, together with a simple algorithm of a central processing unit. As for the method for monitoring water quality, it comprises using a central processing unit to derive the calcium hardness and M alkalinity from a linear functional relation between calcium hardness and specific conductivity, and between log values of M alkalinity and the pH values, and simplifying the temperature curve into a formula to directly produce a saturation index for monitoring water quality. With the aid of mathematical equations for experiment and testing purposes provided by the present invention, the M alkalinity and pH value, as well as the relation between calcium hardness and specific conductivity may be quickly obtained. Therefore, the central processing unit can be used to instantly process the obtained saturation index.

BRIEF DESCRIPTION OF THE DRAWINGS

The foregoing and other features and advantages of the present invention will be more clearly understood from the following detailed description and the accompanying drawings, in which.

FIGS. 2 and 3 are diagrams illustrating the linear relations of Examples using chemically prepared solutions according to the method of the present invention, in which

FIGS. 4 and 5 are diagrams showing the linear relation of Examples using water of pilot cooling tower as an object of simulation, in which

DETAILED DESCRIPTION OF THE PREFERRED EMBODIMENTS

Figure 1:
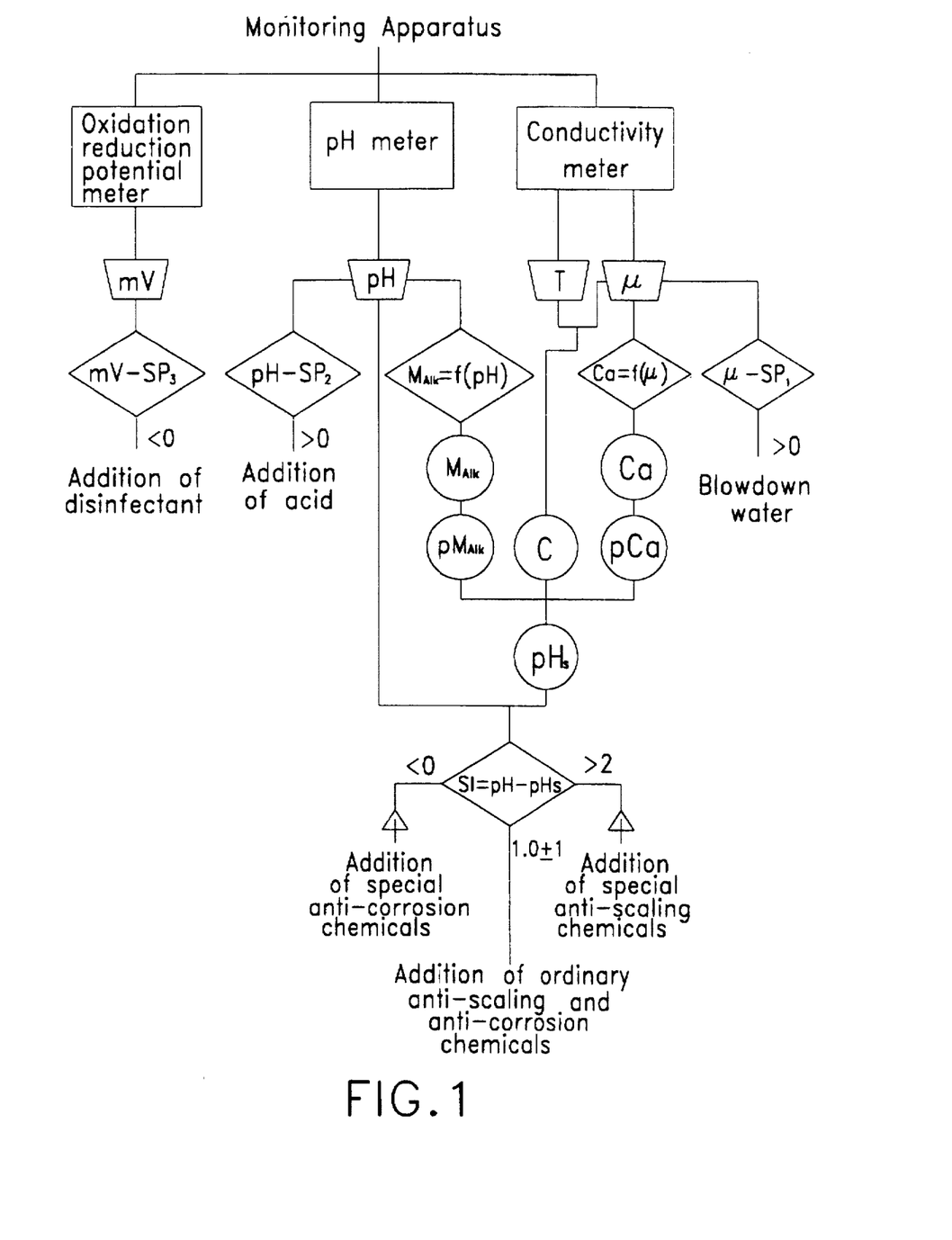
FIG. 1 is a flow chart of the method for water quality monitoring according to the present invention.
Figure 2:
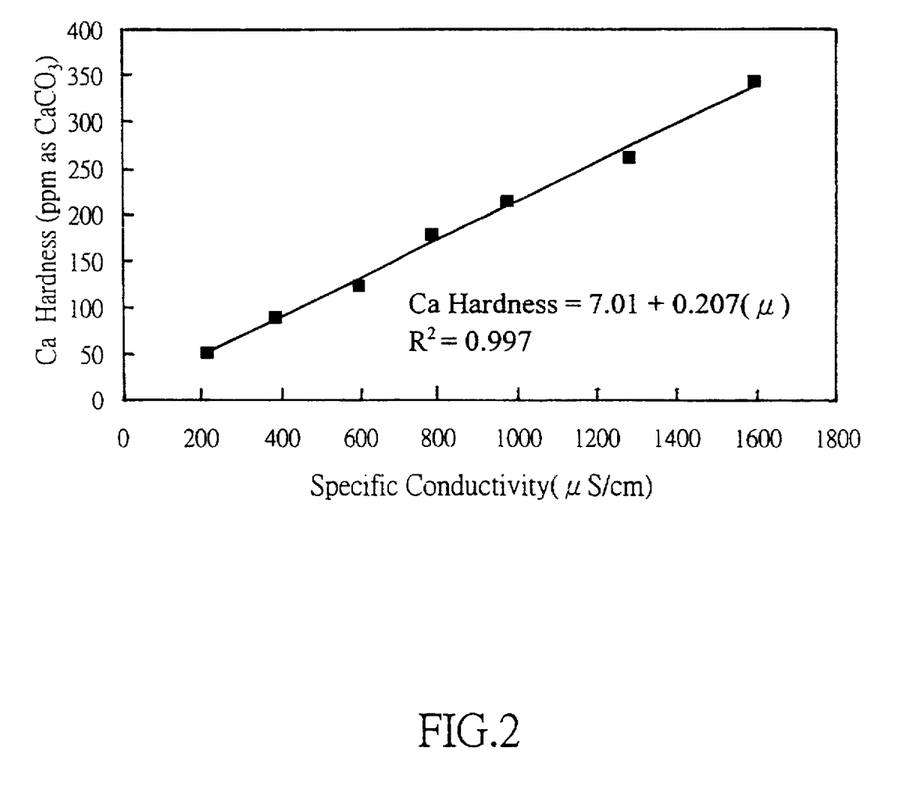
FIG. 2 is a correction curve of the calcium hardness and specific conductivity.

As shown in FIG. 1, with cross reference to FIG. 2, the method according to the present invention essentially comprises obtaining a saturation index by conversion of values obtained by a pH meter and a conductivity meter using mathematical equations. Certainly, as with the prior devices, the automatic water quality monitoring device of the present invention may, in application: (1) utilize an oxidation reduction potential meter to test water quality so as to determine whether addition of disinfectant is necessary; (2) test the pH value of water using a pH meter and compare the obtained pH value with a control set value so as to determine whether addition of sulfuric acid for lowering the pH value is necessary; and (3) test water quality with an conductivity meter so that, when the tested specific conductivity (µS/cm) is greater than a set value, a solenoid valve may be opened instantly to allow discharge of cooling water and then addition of makeup water to reduce the specific conductivity.

Furthermore, the temperature (T) and specific conductivity (µ) obtained by the conductivity meter may be utilized to arrive at a temperature constant (C) using the following equation:

$$C=c_1[log(\mu/2)]-c_2T+c_3$$

This equation is simplified from the temperature constant curve of the Langelier Saturation Index Chart (see page 180 of Betz Handbook of Industrial Water Conditioning, 7th edition, 1976), wherein $c_1$, $c_2$, and $c_3$ are constants, and $c_1=0.1038$; $c_2=0.0189$; and $c_3=2.3681$.

At the same time, M alkalinity may be derived from the tested pH value using the following equation:

$$log[M_{Alk}]_{ppm}=(a \times pH)-b$$

wherein a, b are constants, and may vary according to the difference in water quality.

After obtaining the M alkalinity, the following negative logarithmic equation:

$$pM_{Alk}=-log[M_{Alk}/5000]$$

Furthermore, the specific conductivity (µ) may be used to derive its relation with calcium hardness in the following equation:

$$[Ca^{2+}]_{ppm}=(c \times \mu)+d$$

wherein c, d are constants and may vary according to the difference in water quality.

Like the above-mentioned constants a and b, the values of constants c and d, as shown in FIGS. 2 to FIG. 5, may be obtained from the test values of water.

The above two mathematical equations have been proven to be feasible from the two Examples described hereinafter.

Method of preparing solutions for experimental use:
1. Phenolphthalene: Dissolve 1 g of phenolphthalene in 60 ml of alcohol, and dilute the solution to 100 ml with deionized water.
2. Methyl orange: Dissolve 0.2 g of methyl orange in hot water. Allow to cool. Filter if necessary. Dilute the cooled solution to 100 ml with deionized water.
3. Calcium hardness standard solution: Dilute a suitable amount of 1000 ppm calcium standard solution to 100 ml with deionized water, so that the calcium hardness (as $CaCO_3$) concentration falls within the range of 50–350 ppm.
4. Calcium bicarbonate standard solution: For 0.1 N $NaHCO_3$—Dissolve 0.84 g of $NaHCO_3$ in deionized water and dilute the solution to 100 ml. For 0.001 N–0.007 N $NaHCO_3$ standard solution, dilute 0.1 N $NaHCO_3$ standard solution with deionized water to 100 ml.

EXAMPLE I

We prepare the calcium hardness standard solution and calcium bicarbonate solution, analyze the calcium hardness, and specific conductivity of a series of calcium hardness standard solution and the M alkalinity and pH value of calcium bicarbonate standard solution. Find out the functional relation between calcium hardness and specific conductivity, and that of M alkalinity and pH value. Two reasonable assumptions are made herein:

1. The relation between calcium hardness and specific conductivity is:
    Ca hardness [ppm as $CaCO_3$]=a+bµ (Specific Conductivity:µS/cm)
2. The relation between M alkalinity and pH value:
    log(M alkalinity)[ppm as $CaCO_3$]=c+d(pH)

It can be inferred from the experimental results whether the linear correlation coefficient is good (>0.95). According to the standard of reliability tolerance of 5% in statistics, if the value of $R^2$ is greater than 0.95, then the two assumptions above may be valid, and the intercept and inclination of the formula can be obtained.

Experimental results (1) Relation between calcium hardness and specific conductivity: Prepare standard solutions of different calcium concentration. Find out the specific conductivity, and the results are:

| Specific Conductivity (µS/cm) | Ca Hardness [ppm as $CaCO_3$] |
| --- | --- |
| 216 | 51 |
| 383 | 89 |
| 595 | 123 |
| 785 | 178 |
| 973 | 214 |
| 1285 | 261 |
| 1593 | 343 |

The linear relation between calcium hardness and specific conductivity is shown in FIG. 2. The linear correlation coefficient is 0.997.

(2) Relation between M alkalinity and pH value: Prepare a standard solution of 0.001 N–0.007 N (Normality) from $NaHCO_3$. Analyze the pH values and M alkalinity, and the results are:

| $NaHCO_3$ [N] | pH Value | M alkalinity [ppm as $CaCO_3$] | log (M alkalinity) |
| --- | --- | --- | --- |
| 0.001 | 8.52 | 53 | 1.72 |
| 0.002 | 8.73 | 100 | 2.00 |
| 0.003 | 8.90 | 153 | 2.18 |
| 0.004 | 8.93 | 203 | 2.31 |
| 0.005 | 8.97 | 252 | 2.40 |
| 0.007 | 8.99 | 349 | 2.54 |

Figure 3:
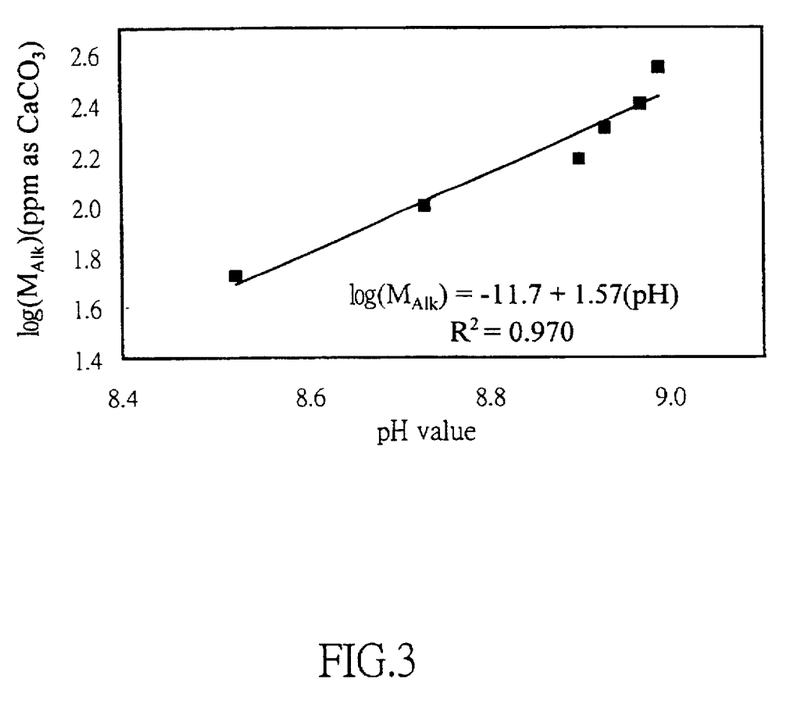
FIG. 3 is a correction curve of the log values of M alkalinity and pH values.

The linear relation between the log values of M alkalinity and pH values is shown in FIG. 3. The linear correlation coefficient is 0.970.

From the foregoing results indicating the relation between calcium hardness and specific conductivity, log values of M alkalinity and pH values, it can be seen that the above functional relation is valid.

EXAMPLE II

Use pilot cooling tower to simulate actual operational conditions. Sample cooling tower circulating water of different cycles of concentration. Test the calcium hardness, specific conductivity, M alkalinity, and pH value. Find out the functional relation between calcium hardness and specific conductivity, and that between M alkalinity and pH value, and whether the value of $R^2$ is greater than 0.95. If $R^2$ is greater than 0.95, then it indicates that there is a functional relation between calcium hardness and specific conductivity, and between M alkalinity and pH value in the pilot cooling tower circulating water sample.

Experimental Results

From concentrated tap water samples simulating cooling tower, obtain circulating water samples of different cycles of concentration and analyze the calcium hardness and specific conductivity. The results are:

| Specific Conductivity (μS/cm) | Ca Hardness [ppm as $CaCO_3$] |
|---|---|
| 442 | 119 |
| 714 | 187 |
| 772 | 193 |
| 778 | 199 |
| 841 | 215 |
| 923 | 240 |

Figure 4:
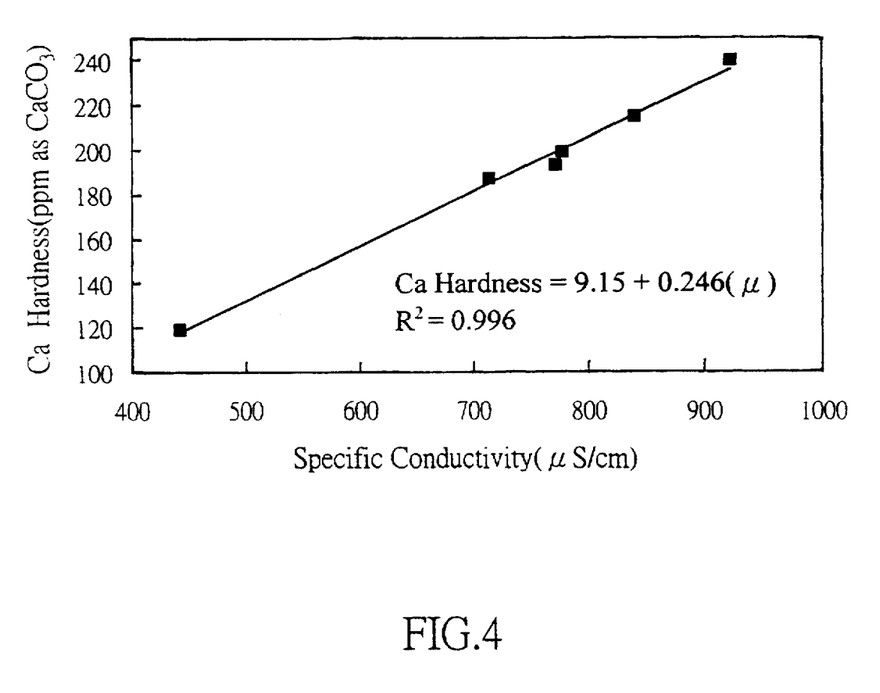
FIG. 4 is similar to FIG. 2.

The linear relation between calcium hardness and specific conductivity is shown in FIG. 4.

At the same time, the results of an analysis of log values of M alkalinity and pH values of the water samples are:

| pH Value | M alkalinity [ppm as $CaCO_3$] | log (M alkalinity) |
|---|---|---|
| 8.29 | 81 | 1.91 |
| 8.55 | 118 | 2.07 |
| 8.56 | 116 | 2.06 |
| 8.57 | 119 | 2.08 |
| 8.59 | 123 | 2.09 |
| 8.60 | 125 | 2.10 |
| 8.62 | 127 | 2.10 |
| 8.64 | 128 | 2.11 |
| 8.66 | 133 | 2.12 |

Figure 5:
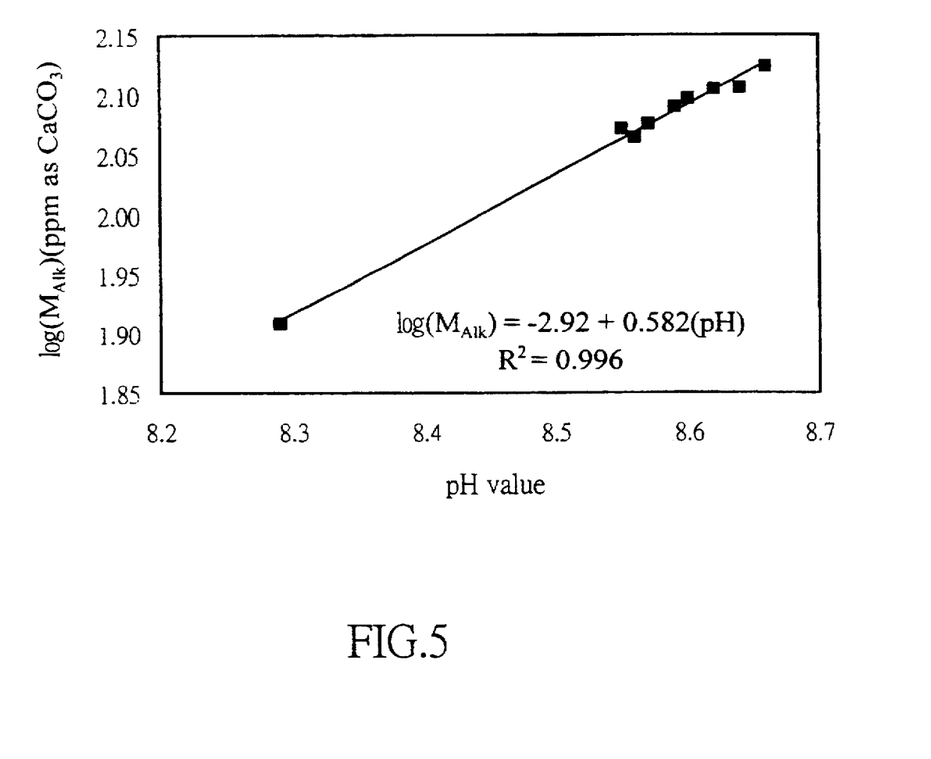
FIG. 5 is similar to FIG. 3.

The linear relation by the above data is shown in FIG. 5.

From FIGS. 4 and 5, it can be proven that, in the actual cooling tower concentrated water samples, the relation between calcium hardness and specific conductivity, and that between log values of M alkalinity and pH values are linear. Therefore, by testing the specific conductivity and the pH value, and converting the tested values using the mathematical equations set out above, the calcium hardness and M alkalinity can be obtained. In actual application, so long as the functional relation between the calcium hardness and specific conductivity and that between the M alkalinity and pH value of different water samples, the calcium hardness and M alkalinity can be obtained utilizing the specific conductivity and pH value.

The M alkalinity negative log index ($pM_{Alk}$), the temperature constant (C), and the calcium hardness negative log index (pCa) obtained above can be substituted into the following equation to find out the pHs:

$$pHs = pCa + pM_{Alk} + C = f(\mu, pH, T)$$

The saturation index (SI) can be obtained by comparing the pH value obtained using the pH meter with pHs. The equation is:

$$SI = pH - pHs$$

Observation shows that when SI is greater than zero, the water quality is prone to precipitation. On the contrary, if the SI value is smaller than zero, the water tends to be corrosive.

Figure 6:
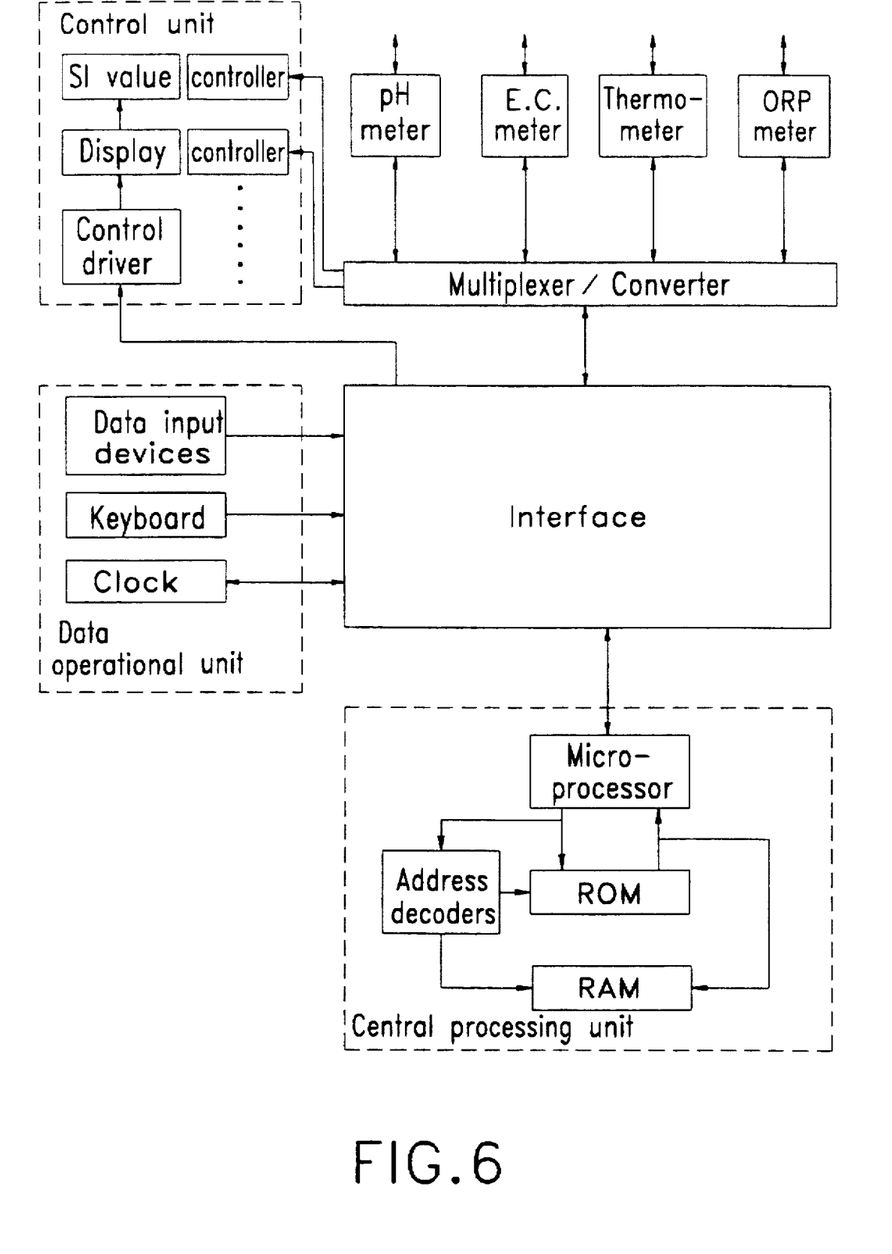
FIG. 6 is a block diagram of a preferred embodiment of the apparatus for monitoring water quality according to the present invention.

As shown by the algorithm in FIG. 6, the values obtained by the pH meter, conductivity meter, thermometer, and even the oxidation reduction potential meter may be converted via a multiplexer by a converter into a signal matching the central processing unit and input via an interface into a microprocessor of the central processing unit. The central processing unit further includes ROM, RAM, address decoders, etc. But as these are not features of the present invention, they are not discussed in detail herein. The above-mentioned constants, set values, and equations may be input into the central processing unit in advance via an operational keyboard or other data key-in devices of a data operational unit for automatic analysis and calculation during water quality testing. And when the value exceeds the set value which is set for control purposes, a controller can send out an alarm, or suitable equipment, such as a metering pump, is driven by the pH meter, oxidation reduction potential meter, or thermometer to instantly add chemicals into the water to improve the water quality. For instance, referring to FIG. 1, when the saturation index value is greater than 2, special anti-scaling chemicals or anti-scaling chemicals of a higher concentration may be added. When the saturation index value is less than zero, special anti-corrosion chemicals or anti-corrosion chemicals of a higher concentration may be added. When the saturation index is between 1.0±1, it is a normal value, then ordinary anti-scaling and anti-corrosion chemicals may be regularly added to the water so that a thin protective layer of scale may be formed on the inner walls of the pipeline.

By means of the method of the present invention, the pH meter, oxidation reduction potential meter, conductivity meter, and special saturation index display can be combined into a single apparatus, which is convenient to operate, inexpensive, and has additional functions. The present invention also uses functional relations, pH values, specific conductivity, and temperature values to obtain such water quality control indices as calcium hardness, M alkalinity, saturation index for enhancing the quality of water quality monitoring and achieving real time control, which indeed benefits water quality monitoring to a great extent.

Although the present invention has been illustrated and described with reference to the preferred embodiments thereof, it should be understood that it is in no way limited to the details of such embodiments, but is capable of numerous modifications within the scope of the appended claims.

What is claimed is:

1. A method for monitoring water quality, comprising the following steps of:

(a) obtaining readings of the temperature and specific conductivity of water so as to find out a temperature constant (C);

(b) obtaining a reading of the pH value of water to derive therefrom the M alkalinity and $PM_{Alk}$;

(c) deriving calcium hardness and pCa value from the specific conductivity of water; and (d) finding out a saturation index (SI) from the constant (C), $PM_{Alk}$ and pCa using the following two equations so as to serve as a reference parameter in scaling inclination and corrosion risks:

$$pHs = pCa + pM_{Alk} + C = f(\mu, pH, T)$$

$$SI = pH - pHs.$$

2. A method for monitoring water quality as claimed in claim 1, wherein the equation of deriving M alkalinity from the pH value is:

$$\log|M_{Alk}|_{ppm}=(a\times pH)-b$$

(wherein a and b are constants)

$$pM_{Alk}=-\log|M_{Alk}/50000|.$$

3. A method for monitoring water quality as claimed in claim 1, wherein the equation of deriving calcium hardness from the specific conductivity is:

$$|Ca^{2+}|_{ppm}=(c\times\mu)+d$$

(wherein c and d are constants)

$$pCa=-\log|Ca^{2+}|+5.$$

4. A method for monitoring water quality as claimed in claim 1, wherein the formula of finding out the value C from the temperature and specific conductivity of water is:

$$C=c_1[\log(\mu/2)]-c_2T+c_3$$

(wherein $c_1$, $c_2$ and $c_3$ are constants).

5. A method for monitoring water quality as claimed in claim 1, wherein the normal saturation index is $1.0\pm1$.

6. A method for monitoring water quality as claimed in claim 4, wherein the temperature constant (C) is obtained from the temperature constant curve of the Langelier Saturation Index Chart.

7. A method for monitoring water quality as claimed in claim 5, wherein when the saturation index (SI) is greater than zero, anti-scaling chemicals of a relatively high concentration or special anti-scaling chemicals can be added.

8. A method for monitoring water quality as claimed in claim 5, wherein when the saturation index (SI) is less than zero, anti-corrosion chemicals of a relatively high concentration or special anti-corrosion chemicals can be added.

9. Multi-purpose apparatus for monitoring water quality, comprising a central processing unit, said central processing unit being connected to a control unit and a data operational unit via an interface circuit, and being connected respectively to a pH value controller, a specific conductivity controller, and a signal output port of a thermometer to obtain the pH value, specific conductivity, and temperature of the water; said central processing unit prestoring programs for obtaining temperature constants (C) using the temperature and specific conductivity, M alkalinity negative log ($pM_{Alk}$) using the pH value, and calcium hardness (pCa) using specific conductivity, and further prestoring the following equations to obtain the saturation index (SI):

$$pHs=pCa+pM_{Alk}+C=f(\mu,pH,T)$$

$$SI=pH-pHs$$

said central processing unit being further provided with a control program in which the normal saturation index value is $1.0\pm1$, whereby when the tested value exceeds the normal value, the control unit will be driven to generate an alarm signal or a controller will be actuated to proceed to meter chemicals into the water.

10. Multipurpose apparatus for monitoring water quality as claimed in claim 9, wherein the equation of M alkalinity derived from the pH value is:

$$\log|M_{Alk}|_{ppm}=(a\times pH)-b$$

(wherein a and b are constants)

$$pM_{Alk}=-\log|M_{Alk}/50000|.$$

11. Multipurpose apparatus for monitoring water quality as claimed in claim 9, wherein the equation of calcium hardness derived from the specific conductivity is:

$$|Ca^{2+}|_{ppm}=(c\times\mu)+d$$

(wherein c and d are constants)

$$pCa=-\log|Ca^{2+}|+5°.$$

12. Multipurpose apparatus for monitoring water quality as claimed in claim 9, wherein the formula of obtaining the value C from the temperature and specific conductivity of water is:

$$C=c_1[\log(\mu/2)]-c_2T+c_3$$

(wherein $c_1$, $c_2$ and $c_3$ are constants).

13. Multipurpose apparatus for monitoring water quality as claimed in claim 9, further comprising an oxidation reduction potential meter for testing water quality and controlling addition of disinfectant.

14. Multipurpose apparatus for monitoring water quality as claimed in claim 9, further comprising a pH meter for testing water quality and controlling addition of acid.

15. Multipurpose apparatus for monitoring water quality as claimed in claim 9, further comprising a conductivity meter for testing water quality and controlling a solenoid valve to discharge cooling water and then let in makeup water.

16. Multipurpose apparatus for monitoring water quality as claimed in claim 9, wherein when the saturation index (SI) is greater than two, anti-scaling chemicals of a relatively high concentration or special anti-scaling chemicals can be added.

17. Multipurpose apparatus for monitoring water quality as claimed in claim 9, wherein when the saturation index (SI) is less than zero, anti-corrosion chemicals of a relatively high concentration or special anti-corrosion chemicals can be added.

* * * * *